United States Patent
Vaders

(10) Patent No.: US 11,413,741 B2
(45) Date of Patent: Aug. 16, 2022

(54) SURGICAL INSTRUMENT HOUSING, AND RELATED SYSTEMS, AND METHODS

(71) Applicant: INTUITIVE SURGICAL OPERATIONS, INC., Sunnyvale, CA (US)

(72) Inventor: Dennis H. Vaders, West Haven, CT (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 17/025,047

(22) Filed: Sep. 18, 2020

(65) Prior Publication Data

US 2021/0138633 A1 May 13, 2021

Related U.S. Application Data

(63) Continuation of application No. 15/569,643, filed as application No. PCT/US2016/029295 on Apr. 26, 2016, now Pat. No. 10,780,573.

(60) Provisional application No. 62/153,242, filed on Apr. 27, 2015.

(51) Int. Cl.
 *B25J 9/00* (2006.01)
 *A61B 34/30* (2016.01)
 (Continued)

(52) U.S. Cl.
 CPC .............. *B25J 9/0009* (2013.01); *A61B 34/30* (2016.02); *A61B 34/35* (2016.02); *A61B 34/37* (2016.02);
 (Continued)

(58) Field of Classification Search
 CPC ..... B25J 9/0009; B25J 15/0019; A61B 34/35; A61B 50/00
 See application file for complete search history.

(56) References Cited

U.S. PATENT DOCUMENTS 5,878,193 A 3/1999 Wang
10,780,573 B2 9/2020 Vaders
(Continued)

FOREIGN PATENT DOCUMENTS

CN 101426412 A 5/2009
CN 101801283 A 8/2010
(Continued)

OTHER PUBLICATIONS

International Search Report and Written Opinion for Application No. PCT/US2016/029295, dated Jul. 26, 2016, 14 pages (ISRG06460/PCT).

(Continued)

*Primary Examiner* — Vicky A Johnson
(74) *Attorney, Agent, or Firm* — Jones Robb, PLLC

(57) ABSTRACT

A force transmission mechanism of a surgical instrument, the force transmission mechanism being configured to releasably engage with a drive interface device located at a patient side cart of a teleoperated surgical system may comprise a housing comprising a side wall surrounding an interior of the housing, one or more drive components in the interior of the housing, a releasable coupling mechanism configured to releasably engage the force transmission mechanism with the drive interface device, wherein the releasable coupling mechanism has a longitudinal axis and is pivotable about an axis oriented approximately perpendicular to the longitudinal axis.

20 Claims, 14 Drawing Sheets

(51) Int. Cl.
*A61B 34/37* (2016.01)
*A61B 34/35* (2016.01)
*B25J 9/16* (2006.01)
*A61B 50/00* (2016.01)
*A61B 90/00* (2016.01)
*A61B 17/00* (2006.01)
*B25J 15/00* (2006.01)

(52) U.S. Cl.
CPC ............. *B25J 9/1689* (2013.01); *A61B 50/00* (2016.02); *A61B 2017/00477* (2013.01); *A61B 2034/302* (2016.02); *A61B 2034/305* (2016.02); *A61B 2090/0813* (2016.02); *B25J 9/0084* (2013.01); *B25J 9/161* (2013.01); *B25J 15/0019* (2013.01); *Y10S 901/02* (2013.01); *Y10S 901/41* (2013.01)

(56) References Cited

U.S. PATENT DOCUMENTS

| | | |
|---|---|---|
| 2002/0128661 A1 | 9/2002 | Brock et al. |
| 2007/0016174 A1 | 1/2007 | Millman et al. |
| 2007/0239120 A1 | 10/2007 | Brock et al. |
| 2013/0211401 A1 | 8/2013 | Bailey et al. |
| 2014/0069437 A1 | 3/2014 | Reis et al. |
| 2014/0296873 A1* | 10/2014 | Morgan ................ A61B 17/32 606/130 |
| 2015/0257841 A1 | 9/2015 | Dachs, II |
| 2016/0151115 A1 | 6/2016 | Karguth et al. |

FOREIGN PATENT DOCUMENTS

| | | |
|---|---|---|
| CN | 102630154 A | 8/2012 |
| WO | WO-2007126443 A2 | 11/2007 |
| WO | WO-2011037394 A2 | 3/2011 |
| WO | WO-2014162217 A1 | 10/2014 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SURGICAL INSTRUMENT HOUSING, AND RELATED SYSTEMS, AND METHODS

RELATED APPLICATIONS

This application is a continuation of U.S. patent application Ser. No. 15/569,643, filed Oct. 26, 2017, which is a national stage application of U.S. PCT Application No. PCT/US2016/029295, filed Apr. 26, 2016, which claims the benefit of U.S. Provisional Patent Application No. 62/153,242, filed Apr. 27, 2015 (now expired), each of which is hereby incorporated by reference in their entirety.

TECHNICAL FIELD

The present disclosure relates to force transmission mechanisms for surgical instruments, and in particular to releasable coupling mechanisms for engaging and disengaging force transmission mechanisms to drive interface components.

INTRODUCTION

Remotely controlled surgical instruments, including teleoperated surgical instruments (e.g., surgical instruments operated at least in part with computer assistance, such as instruments operated with robotic technology) and/or manually operated surgical instruments, are often used in minimally invasive medical procedures. During medical procedures, motion of the surgical instruments may be actuated by a mechanical force transmission mechanism at a proximal end of the surgical instrument shaft. The force transmission mechanism generally receives input (e.g., either via a teleoperated surgical system or through manual input) and acts on actuation elements that extend from the transmission mechanism down the shaft (and through a wrist, when applicable) of the surgical instrument. The actuation elements in turn actuate portions of the surgical instrument, such as to orient and position an end effector located at a distal end of the surgical instrument. The surgical instrument may further include a wrist, such as a jointed, articulatable structure, that the end effector is connected to so that the end effector may be oriented and positioned relative to the shaft.

A force transmission mechanism of a surgical instrument may include a chassis and a housing. The force transmission mechanism may interface with various actuation drives, such as, for example, actuation drives of a patient side cart of a teleoperated surgical system. In particular, actuation drives interface with, for example, drive inputs of the force transmission mechanism either directly or through a sterile adapter disposed between the drive inputs of force transmission mechanism and the actuation drives. It is desirable, for example, for the force transmission mechanism to include a coupling mechanism to facilitate connecting or disconnecting the force transmission mechanism to another component, such as the sterile adapter or directly with another drive interface component. Further, it is desirable, for example, to arrange and configure the coupling mechanism to be relatively easy to use when coupling and uncoupling the surgical instrument to a drive interface component, and also to conserve space for other components of the force transmission mechanism.

SUMMARY

Exemplary embodiments of the present disclosure demonstrate one or more of the above-mentioned desirable features. Other features and/or advantages may become apparent from the description that follows.

In accordance with at least one exemplary embodiment, a force transmission mechanism of a surgical instrument, which is configured to releasably engage with a drive interface device located at a patient side cart of a teleoperated surgical system, comprises a housing. The housing is configured to cover one or more drive components of the force transmission mechanism. The housing comprises a releasable coupling mechanism configured to releasably engage with the drive interface device. The housing and the releasable coupling mechanism are a monolithic construction.

In accordance with at least one exemplary embodiment, a method of manufacturing a housing for a force transmission mechanism of a surgical instrument, the housing being configured to cover one or more drive components of the force transmission mechanism, the force transmission mechanism being configured to engage with a drive interface device to remotely actuate the surgical instrument, the method comprises molding, as a monolithic structure, the housing with a releasable coupling mechanism configured to releasably engage with a drive interface device of a surgical system. The releasable engagement permits releasable coupling of the surgical instrument to the drive interface device.

In accordance with at least one exemplary embodiment, a teleoperated surgical system comprises a drive interface device and a surgical instrument. The drive interface device is configured to be controlled via input commands transmitted from a user input mechanism situated remotely from the drive interface device. The surgical instrument comprises a shaft, and an end effector located at a distal end of the shaft, and a force transmission mechanism located at a proximal end of the shaft. The force transmission mechanism comprises a housing having a releasable coupling mechanism releasably engageable with the drive interface device. The housing and the releasable coupling mechanism are a monolithic construction. The force transmission mechanism further comprises one or more drive components configured, in an engaged state of the housing with the drive interface device, to be driven by the drive interface device so as to actuate the end effector. The one or more drive components are enclosed by the housing.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
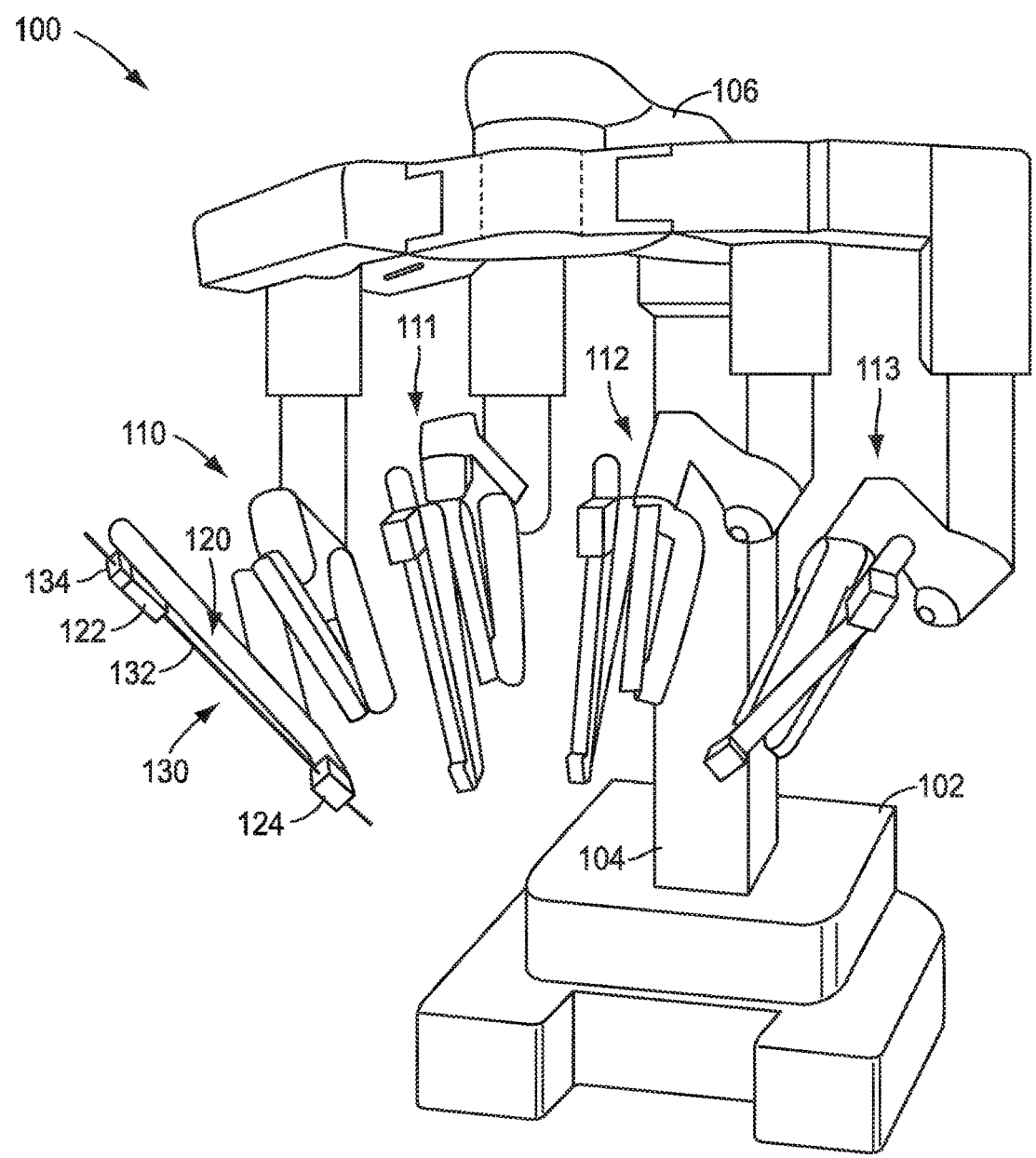
FIG. 1 is a perspective view of a patient side cart of a teleoperated surgical system, according to an exemplary embodiment.

This description and the accompanying drawings that illustrate exemplary embodiments should not be taken as limiting. Various mechanical, compositional, structural, electrical, and operational changes may be made without departing from the scope of this description and claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

In accordance with various exemplary embodiments, the present disclosure contemplates force transmission mechanisms that include releasable coupling mechanisms to facilitate coupling and release of the force transmission mechanism from a drive interface device. Such releasable couplings can facilitate coupling of the force transmission mechanism to a manipulator of a patient side cart in a teleoperated surgical system. As described further below, the releasable couplings can couple to a sterile adapter disposed between a force transmission mechanism and an actuation interface assembly of a patient side cart manipulator or can couple directly to the actuation interface assembly of the manipulator.

Various exemplary embodiments described herein further contemplate systems and surgical instruments including such force transmission mechanisms and methods of manufacturing the force transmission mechanisms. For example, at least a portion of the releasable coupling mechanism can be incorporated into a housing of the force transmission mechanism, which can facilitate manufacture by avoiding a construction that includes multiple parts to be assembled. According to an exemplary embodiment, the housing and the releasable coupling mechanism are made together as a single piece, monolithic construction.

Force transmission housings with releasable couplings according to exemplary embodiments are relatively easy to operate, for example, so as to permit one-handed connecting and disconnecting of the surgical instrument to a drive interface device. Further, embodiments of the present disclosure contemplate arranging the releasable coupling mechanisms as part of the force transmission housing such that those components do not intrude upon space on the force transmission chassis that may be valuable for locating other drive components. In minimally invasive surgical instruments, achieving such conservation of space can be difficult and is desirable.

Referring now to FIG. 1, an exemplary embodiment of a patient side cart 100 of a teleoperated surgical system is shown. A teleoperated surgical system further includes a surgeon console (not shown) for receiving input from a user to control instruments mounted at patient side cart 100. A teleoperated surgical system also can include an auxiliary equipment/vision cart (not shown), which optionally includes at least part of the system's computer control equipment and/or light source for endoscopic imaging control. Further, the exemplary embodiments described herein may be used, for example, with a da Vinci® Surgical System, such as the da Vinci Si® Surgical System, or the da Vinci Xi® Surgical System, both with or without Single-Site® single orifice surgery technology, all commercialized by Intuitive Surgical, Inc.

Patient side cart 100 includes a base 102, a main column 104, and a main boom 106 connected to main column 104. Patient side cart 100 also includes a plurality of teleoperated manipulator arms 110, 111, 112, 113 (sometimes referred to as patient side manipulators (PSMs) or manipulators), which are each connected to main boom 106. Manipulator arms 110, 111, 112, 113 each include an instrument mount portion 120 to which an instrument 130 is mounted, which is illustrated as being attached to manipulator arm 110. Portions of manipulator arms 110, 111, 112, 113 are manipulated during a surgical procedure according to commands provided by a user at the surgeon console. In an exemplary embodiment, signal(s) or input(s) transmitted from a surgeon console are transmitted to the control/vision cart, which interpret the input(s) and generate command(s) or output(s) to be transmitted to the patient side cart 100, for example through drive interface devices and ultimately to the surgical instrument transmission mechanism, to cause manipulation of an instrument 130 (only one such instrument being mounted in FIG. 1) and/or portions of manipulator arm 110 to which the instrument 130 is coupled at the patient side cart 100.

Instrument mount portion 120 comprises an actuation interface assembly 122 and a cannula mount 124. A shaft 132 of instrument 130 extends through cannula mount 124 (and on to a surgery site during a surgical procedure). A force transmission mechanism 134 of instrument 130 is mechanically coupled with the actuation interface assembly 122, according to an exemplary embodiment. Cannula mount 124 is configured to hold a cannula (not shown in FIG. 1) through which shaft 132 of instrument 130 may extend to a surgery site during a surgical procedure. Actuation interface assembly 122 contains a variety of drives (e.g., servo-operated output drives) and other mechanisms that are controlled to respond to input commands at the surgeon console and transmit forces to the force transmission mechanism 134 to actuate instrument 130, as those skilled in the art are familiar with, and thus can be broadly classified as a drive interface device. For instance, the output drives of actuation interface assembly 122 directly engage with interface structures (not shown) of force transmission mechanism 134 and transmit forces to force transmission mechanism 134, as will be discussed further below.

Although the exemplary embodiment of FIG. 1 shows an instrument 130 attached to only manipulator arm 110 for ease of illustration, an instrument may be attached to any and each of manipulator arms 110, 111, 112, 113. An instrument 130 may be a surgical instrument with an end effector or may be an endoscopic imaging instrument or other sensing instrument utilized during a surgical procedure to provide information, (e.g., visualization, electrophysiological activity, pressure, fluid flow, and/or other sensed data) about a remote surgical site and/or its surroundings. In the exemplary embodiment of FIG. 1, a surgical instrument with an end effector or an imaging instrument may be attached to and used with any of manipulator arms 110, 111, 112, 113. However, the embodiments described herein are not limited to the exemplary embodiment of the patient side cart of FIG. 1 and various other teleoperated surgical system configurations, including patient side cart configurations, may be used with the exemplary embodiments described herein.

Figure 2:
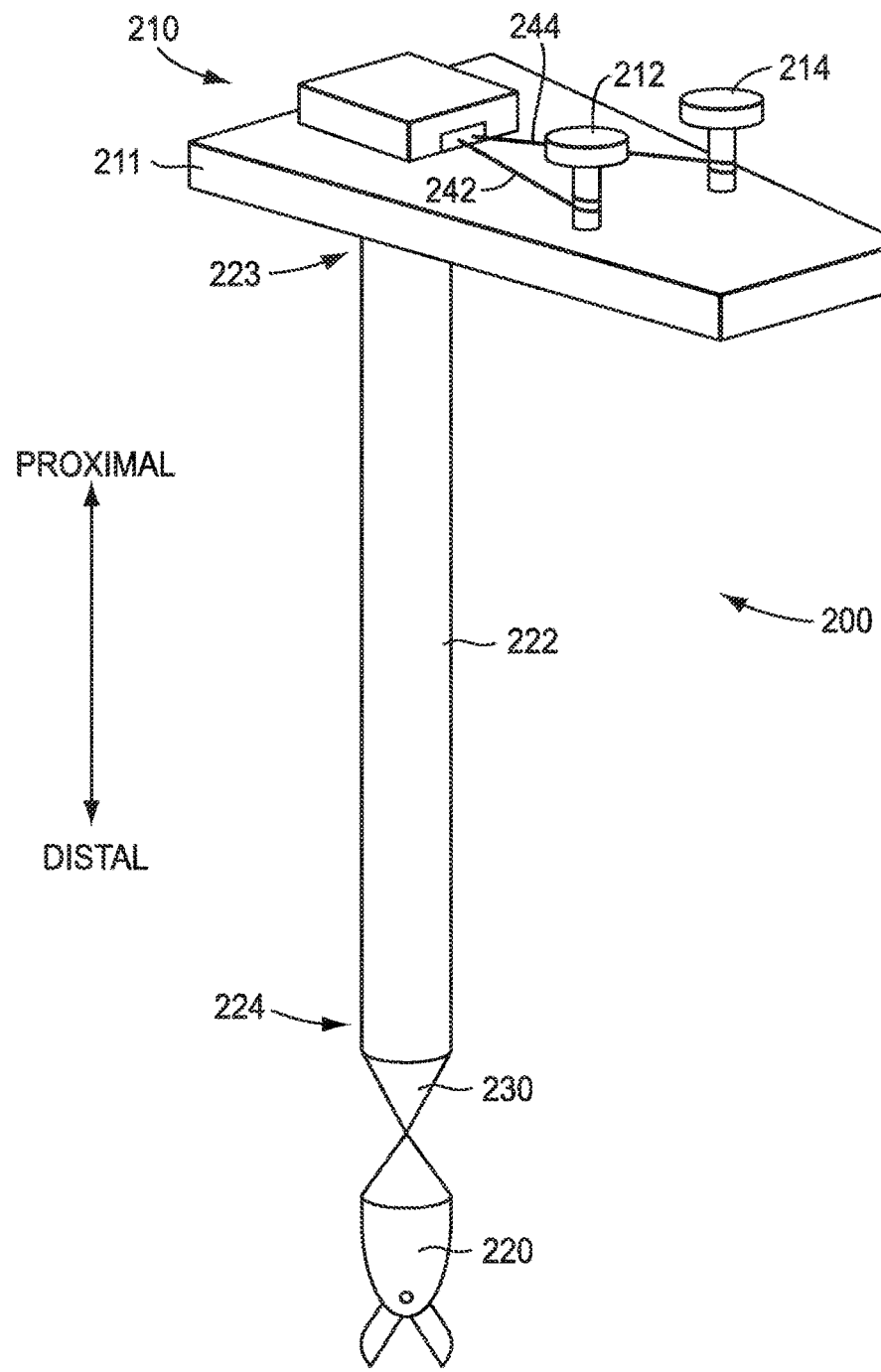
FIG. 2 shows a diagrammatic perspective view of a portion of a surgical instrument, according to an exemplary embodiment.

Turning to FIG. 2, a schematic side view of an exemplary embodiment of a surgical instrument 200 is shown. For instance, surgical instrument 200 may be used as instrument 130 with the patient side cart 100 of the exemplary embodiment of FIG. 1. Surgical instrument 200 includes a force transmission mechanism 210 (a chassis 211 which is shown in the exemplary embodiment of FIG. 2, with a housing not being shown to reveal components of the force transmission mechanism 210 within), a shaft 222 connected to force transmission mechanism 210 at a proximal end 223 of shaft 222, a wrist 230 connected to a distal end 224 of shaft 222, and an end effector 220 connected to wrist 230. According to an exemplary embodiment, shaft 222 is flexible. Various diameters for shaft 222 exist in a range suitable for minimally invasive surgery. According to an exemplary embodiment, shaft 222 has a diameter ranging from about 3 mm to about 15 mm. For example, shaft 222 has a diameter of 3 mm, 5 mm, 8 mm, 13 mm, or 15 mm. According to another exemplary embodiment, the diameter of shaft 222 ranges, for example, from about 5 mm to about 8 mm. End effector 220 can have a variety of configurations, including, but not limited to, for example, forceps, a needle driver for suturing, cutting devices, ablation devices, dissecting devices, clip appliers, and other end effector configurations for performing various surgical procedures.

Surgical instrument 200 includes one or more members to transmit force between force transmission mechanism 210 and end effector 220 and/or between force transmission mechanism 210 and an optional wrist or joint mechanism 230. For example, actuation elements 242, 244 connect force transmission mechanism 210 to end effector 220 to provide actuation forces to end effector 220, such as by extending through an interior of shaft 222. By utilizing actuation elements 242, 244, force transmission mechanism 210 transmits mechanical forces along the shaft to actuate end effector 220 to control, for example, a jaw of end effector 220 (or other moveable part of end effector 220). In another example, actuation elements 242, 244 are used to actuate wrist 230 in one or more orientation degrees of freedom (e.g. pitch and/or yaw). Actuation elements 242, 244 may be tension elements, such as when force transmission mechanism 210 is a pull-pull mechanism, or one or more actuation element rods or push rods, tubes, or cables, such as when force transmission mechanism 110 is a push-pull mechanism.

Force transmission mechanism 210 includes one or more components to engage with a patient side cart of a teleoperated surgical system, for example, through one or more drive interface devices, to transmit a force provided by patient side cart to surgical instrument 100 of the exemplary embodiment of FIG. 1. Persons skilled in the art will be familiar with surgical instrument force transmission mechanisms, which receive a mechanical input force from a power source (e.g., an electric motor from a manipulator supporting the instrument) and convert and/or redirect the received force to an output force to drive a component (e.g., a wrist, and end effector) on the instrument. For example, force transmission mechanism 210 connects with the actuation interface assembly 122 of the patient side cart 100 of the exemplary embodiment of FIG. 1 so actuation interface assembly 122 acts as a drive interface device that transmits forces to drive components of force transmission mechanism 210 to actuate instrument 200. According to an exemplary embodiment, force transmission mechanism 210 includes one or more actuation input mechanisms 212, 214 that engage with a manipulator of a patient side cart, such as actuation interface assembly 122 of patient side cart 100. According to another exemplary embodiment, actuation input mechanisms 212, 214 interact with a manipulator of a patient side cart, such as actuation interface assembly 122 of patient side cart 100, via a drive interface device that serves as a boundary for a sterile field (e.g., a sterile adapter, not shown) and is disposed intermediate the force transmission mechanism 210 and the actuation interface assembly 122 of patient side cart 100, as will be described below.

When force transmission mechanism 210 is a pull-pull mechanism and actuation elements 242, 244 are tension elements, actuation input mechanisms 212, 214, for example, can be capstans that are rotationally driven by actuation interface assembly 122 to tension actuation elements 242, 244 and actuate instrument. Thus, actuation input mechanisms 212, 214 utilize actuation forces from an actuation interface assembly to actuate instrument 200. Force transmission mechanism 210 may include other actuation input mechanisms to receive a force input to force transmission mechanism 210 and actuate various functionalities of a surgical instrument, such as, for example, gears, clutches, rods, levers, and other mechanisms familiar to one ordinary skill in the art. Further, force transmission mechanism 210 may include other numbers of actuation input mechanisms 212, 214 than shown in the exemplary embodiment of FIG. 2, such as, for example, one, three, four, five, or more actuation input mechanisms.

Figure 3:
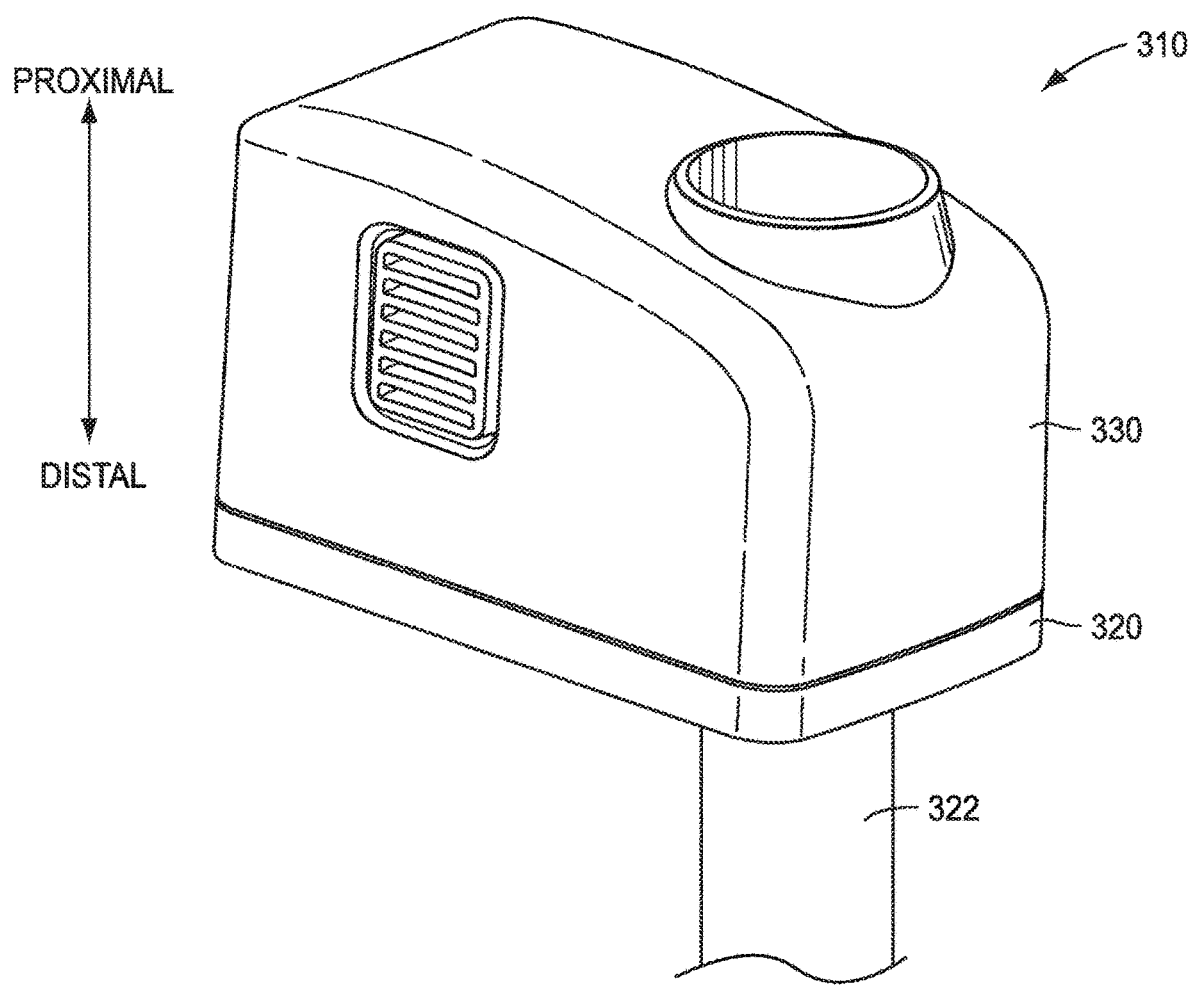
FIG. 3 is a partial view of a surgical instrument including a transmission mechanism, according to an exemplary embodiment.

Turning to FIG. 3, a portion of a surgical instrument is shown, which includes a force transmission mechanism 310 and a proximal portion of an instrument shaft 322 that is connected to, and extends in a distal direction from, the force transmission mechanism 310. Shaft 322 may be configured according to the exemplary embodiments of FIGS. 1 and 2 and may extend from force transmission mechanism 310 along a proximal-distal direction, as depicted in FIG. 3. Force transmission mechanism 310 may be coupled with an actuation interface assembly of a manipulator arm, such as via the actuation interface assembly 122 of the exemplary embodiment of FIG. 1, to receive forces from the actuation interface assembly for actuating the instrument, such as via actuation input mechanisms 212, 214 of the exemplary embodiment of FIG. 2.

As shown in the exemplary embodiment of FIG. 3, force transmission mechanism 310 comprises a housing 330 and a chassis 320 coupled to one another. Although various exemplary embodiments are described herein with chassis 320 and housing 330 being separate pieces connected to one another, the various exemplary embodiments described herein contemplate a force transmission mechanism in which chassis 320 and housing 330 have a single-piece construction. According to an exemplary embodiment, chassis 320 serves as a platform upon which components of force transmission mechanism 310 are mounted, such as, for example, actuation input mechanisms 212, 214 and actuation elements 242, 242 of the exemplary embodiment of FIG. 2, with housing 330 coupling with chassis 320 to complete the enclosure of force transmission mechanism 310.

Figure 4:
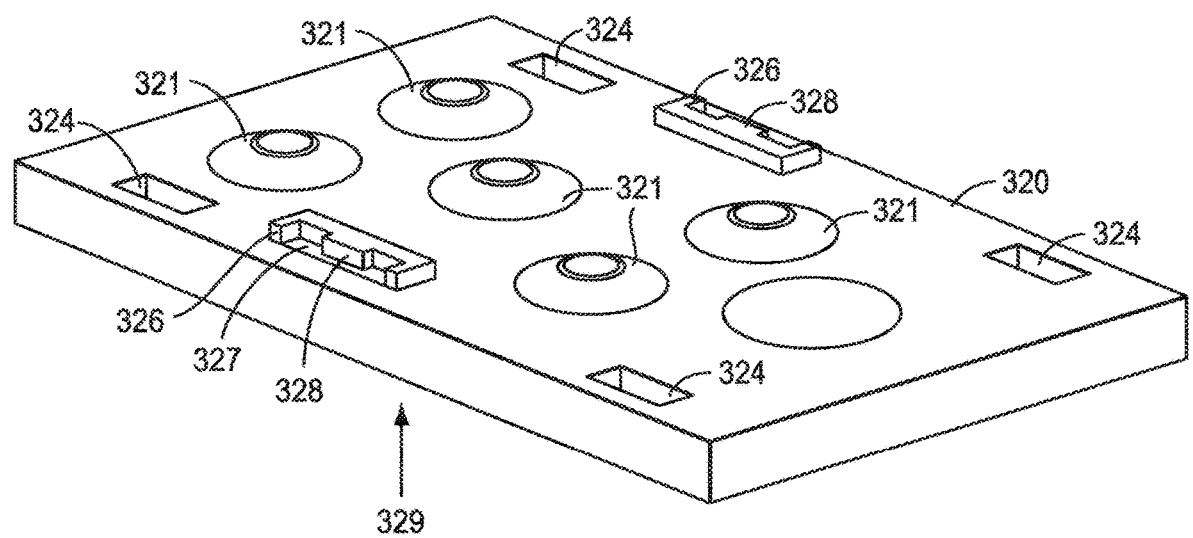
FIG. 4 is a diagrammatic perspective view of a chassis of a force transmission mechanism, according to an exemplary embodiment.

As depicted in FIG. 4, which shows chassis 320 in isolation (with components, such as actuation input mechanisms and actuation elements of force transmission mechanism 310 not being shown to facilitate viewing of chassis 320), chassis 320 comprises one or more compartment(s) 321 that each houses an interface structure that couples with a corresponding interface drive mechanism of a drive interface device. As shown in the exemplary embodiment of FIG. 5, chassis 320 includes one or more interface structures 323, which may correspond in number to the one or more compartment(s) 321. Interface structures 323 are coupled to actuation input mechanisms (e.g., actuation input mechanisms 212, 214 of FIG. 2) to transmit forces received from an interface drive device and drive actuation elements (e.g., actuation elements 242, 244 of FIG. 2) of a force transmission mechanism.

Figure 5:
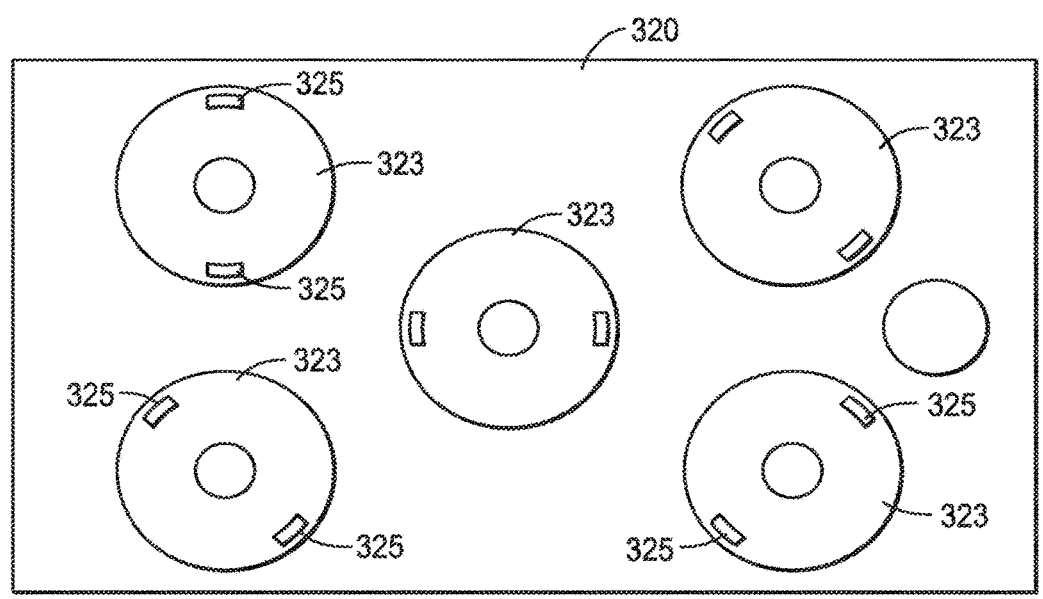
FIG. 5 is a bottom view of the chassis of FIG. 4.

Interface structures 323 may be configured as, for example, disks, as depicted in the exemplary embodiment of FIG. 5. Interface structures may include structures to facilitate coupling between interfaces structures and interface drive mechanisms of an interface drive device. For example, interface structures 323 include recesses 325, sized to receive protrusions (not shown) of a corresponding drive interface device, as will be discussed below, to facilitate coupling between the drive interface device and interface structures 323. According to another exemplary embodiment, the locations of the recesses 325 and protrusions are reversed, with interface structures 323 including the protrusions and the drive interface device including recesses 325 to receive the protrusions.

Figure 6:
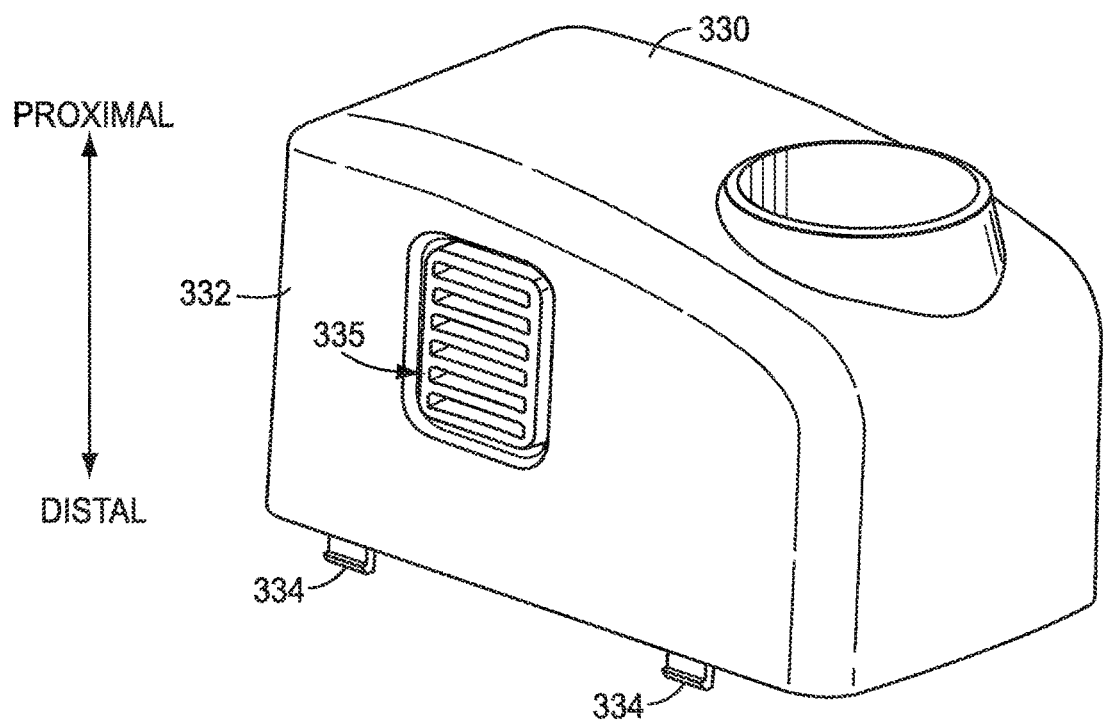
FIG. 6 is a perspective view of a housing of a force transmission mechanism, according to an exemplary embodiment.

FIG. 6 illustrates an exemplary embodiment of a force transmission mechanism housing 330 of force transmission mechanism 310 of FIG. 3, according to an exemplary embodiment. Housing 330 and chassis 320 may include connector structures to couple housing 330 and chassis 320 to one another, such as when housing 330 and chassis 320 are provided as separate pieces. According to an exemplary embodiment, structures to connect housing 330 and chassis 320 are separate from a releasable coupling mechanism to couple force transmission mechanism 310 to a drive interface device, which will be discussed further below. According to an exemplary embodiment, at least a portion of a connector to couple housing 330 and chassis 320 has a one-piece (i.e., monolithic) construction with housing 330. For example, housing 330 includes one or more housing connector structures 334, as shown in the exemplary embodiment of FIG. 6. As indicated in the exemplary embodiment of FIGS. 6 and 7, connector structures 334 are manufactured to have a single-piece (i.e., monolithic) construction with housing 330, such as with side wall 332 of housing 330. As a result, the force transmission mechanism can be efficiently manufactured without further assembly of connector structures 334 with housing 330, as may be required if connector structures are made as structures separate from the housing 330. Of course those having ordinary skill in the art would appreciate that the scope of the present disclosure is not limited to the connector structures 334 being monolithically made as a single-piece construction with the rest of housing 330, and instead could be made separately and joined to the housing 330 via any suitable joining technique.

Chassis 320 may include one or more corresponding connector structures to engage with connector structures of the housing 330. For example, chassis 320 includes recesses 324, as shown in the exemplary embodiment of FIG. 4, to receive corresponding connector structures 334 of housing 330. In various exemplary embodiments, connector structures 334 are, for example, hook-type fasteners that are inserted within recesses 324 to engage chassis 320 to couple housing 330 and chassis 320 to one another. However, other types of complementary connector structures can be used to connect the chassis 320 and housing 330 together. Further, the connector structures shown and described can be reversed in their relative positioning on the chassis and the housing.

According to an exemplary embodiment, a drive interface device can be configured to provide a sterile boundary between the surgical instrument and the manipulator of patient side cart. Such a drive interface device may be coupled to the force transmission mechanism of a surgical instrument and in turn to the actuation interface assembly to serve as a boundary at the patient side cart that separates a sterile region and non-sterile region during a surgical procedure. For example, interface drive mechanisms of a sterile adapter engage with input drives of an actuation interface assembly and also engage with interface structures of a force transmission mechanism so that forces provided by the actuation interface assembly are transmitted to the force transmission mechanism through the sterile adapter.

Figure 8:
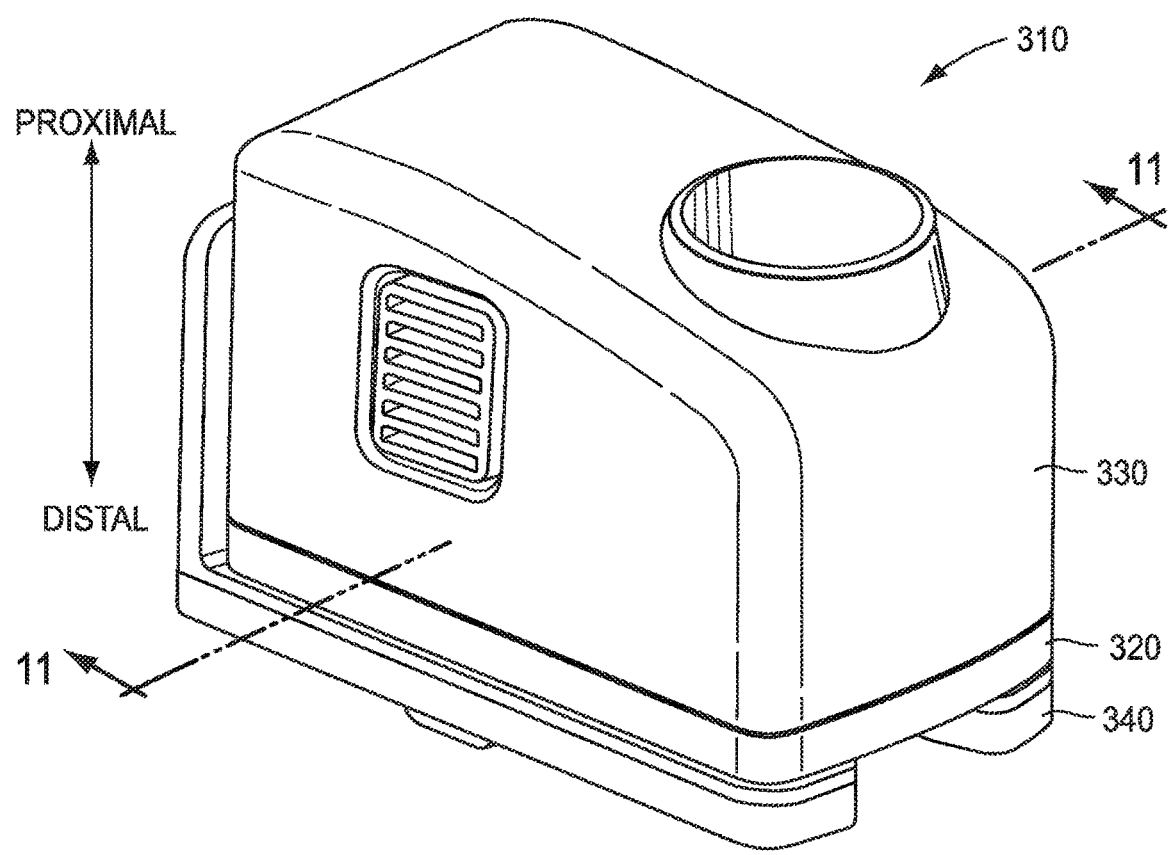
FIG. 8 is a perspective view of a force transmission mechanism coupled to a sterile adapter, according to an exemplary embodiment.
Figure 9:
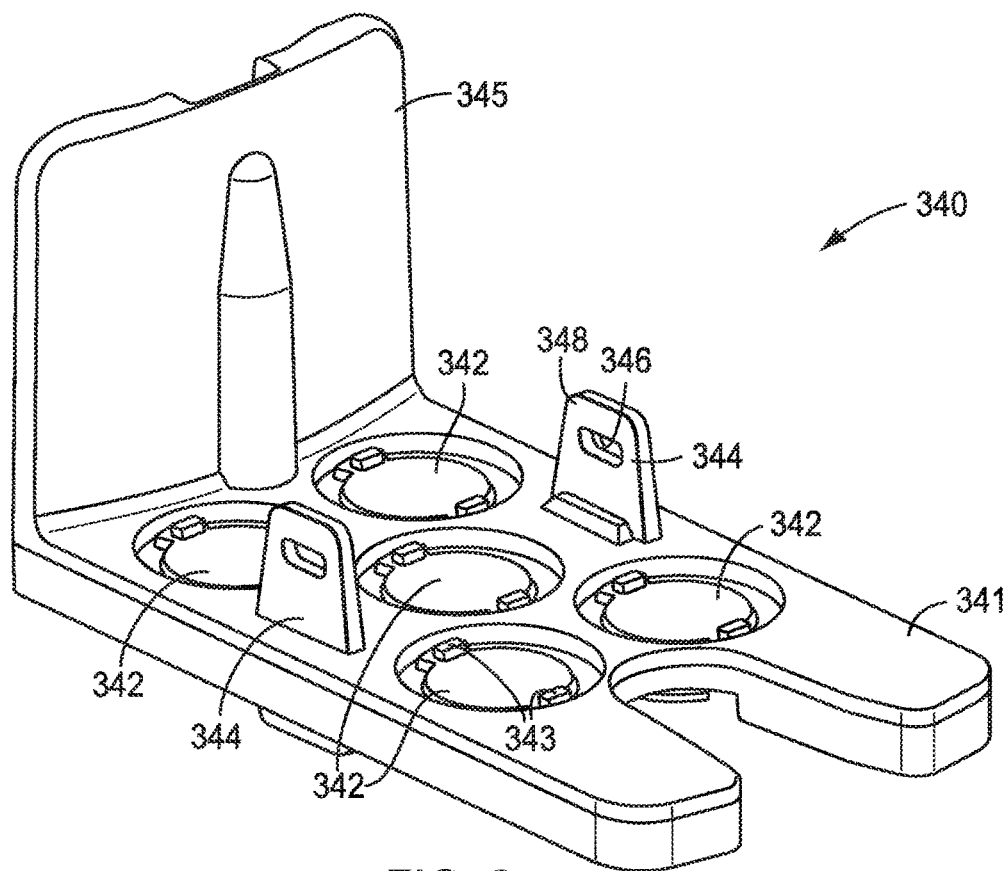
FIG. 9 is a perspective view of a sterile adapter, according to an exemplary embodiment.

As shown in the exemplary embodiment of FIG. 8, a sterile adapter 340 is connected to force transmission mechanism 310. Sterile adapter 340 may function as a drive interface device that couples force transmission mechanism 310 to a manipulator (e.g., actuation interface assembly 122 of patient side cart 100 of FIG. 1). Sterile adapter 340 also can be attached to a surgical drape (not shown) to define a sterile region and non-sterile region during a surgical procedure, according to an exemplary embodiment. Turning to FIG. 9, an exemplary embodiment of a sterile adapter 340 is shown in isolation, disconnected from the surgical instrument and from an actuation interface assembly of a patient side cart. According to the exemplary embodiment of FIG. 9, sterile adapter 340 includes a base 341 and one or more interface drive mechanisms 342 configured on one side to engage with the drive inputs of a force transmission mechanism and on the other side to engage with the actuation interface assembly (e.g., output drives of an actuation interface assembly). Sterile adapter 340 further includes a flange 345, although the various exemplary embodiments described herein are not limited to sterile adapters that include flange 345. According to an exemplary embodiment, flange 345 is connected to a surgical drape (not shown) and guides the surgical drape along a portion of a manipulator arm of a patient side cart to which the sterile adapter 340 is coupled. Further, flange 345 guides and aligns force transmission mechanism 310 when force transmission mechanism 310 is being connected to sterile adapter 340.

As discussed above with regard to the exemplary embodiments of FIGS. 1 and 2, a force transmission mechanism of an instrument (e.g., force transmission mechanisms 134, 210 of FIGS. 1 and 2) directly couples with an actuation interface assembly (e.g., actuation interface assembly 122 of FIG. 1) so the force transmission mechanism receives forces from the actuation interface assembly to actuate the instrument. According to another exemplary embodiment, a sterile adapter couples with an actuation interface assembly to receive forces from the actuation interface assembly and transmit the forces to the force transmission mechanism. Thus, the sterile adapter provides a barrier between a sterile region on the side of actuation interface assembly and a non-sterile region on the side of the force transmission mechanism.

For example, sterile adapter 340 is disposed between force transmission mechanism 310 and an actuation interface assembly of a manipulator arm, such as actuation interface assembly 122 of FIG. 1. Interface drive mechanism(s) 342 of sterile adapter 340 engage with the actuation interface assembly (e.g., output drives of the actuation interface assembly) and transmit forces received from the actuation interface assembly to corresponding interface structures 323 of force transmission mechanism 310. As discussed above with regard to the exemplary embodiment of FIG. 5, interface drive mechanism(s) 342 includes, for example, structures configured to engage with corresponding interface structures 323 of force transmission mechanism 310 to facilitate transmission of forces between sterile adapter 340 and force transmission mechanism 310. According to an exemplary embodiment, interface drive mechanism(s) 342 of sterile adapter 340 includes protrusions 343 configured to couple with corresponding and complementary recesses 325 of the interface structure(s) 323 of force transmission mechanism 310 so that the interface drive mechanism(s) 342 of sterile adapter 340 and interface structures 323 of force transmission mechanism 310 move (e.g., rotate) together. According to an exemplary embodiment, interface drive mechanism(s) 342 includes structures configured to couple with corresponding and complementary structures of output drive(s) of an actuation interface assembly of a manipulator arm, such as when force transmission mechanism 310 couples directly with an actuation interface assembly.

Figure 10:
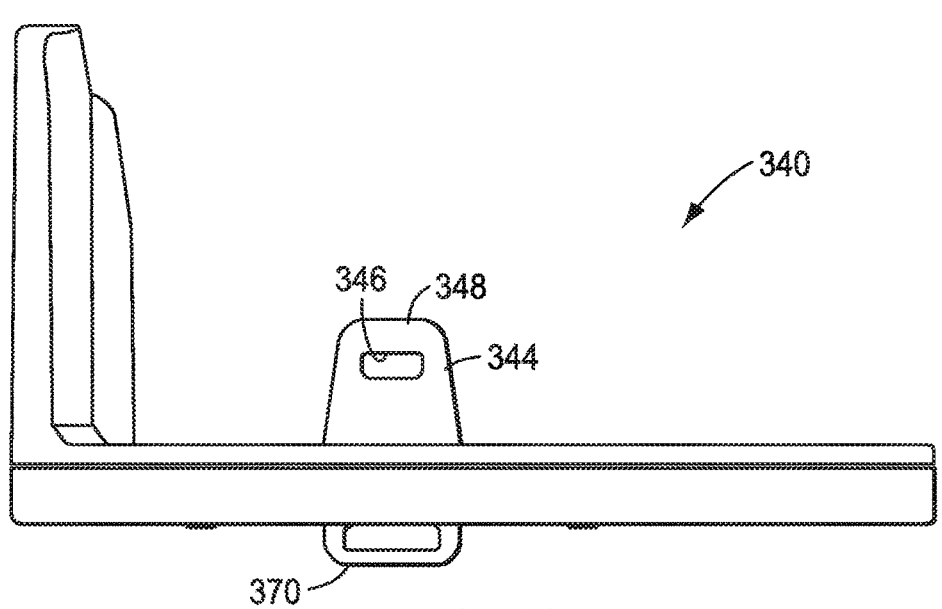
FIG. 10 is a side view of the sterile adapter of FIG. 9.

Sterile adapters in accordance with various exemplary embodiments can include one or more structures for releasably coupling the sterile adapters to a force transmission mechanism. For example, sterile adapter 340 includes one or more fastener members 344. Fastener members 344 include, for example, tabs disposed toward an outer periphery of the sterile adapter based 341. In the exemplary embodiment of FIG. 9, fastener members 344 include a mating feature, for example, an aperture 346, configured to receive a corresponding mating feature of a fastener member of force transmission mechanism 310, as will be described below. Although fastener members 344 are depicted as including an aperture 346 that passes completely through the fastener member 344 in the exemplary embodiment of FIGS. 9 and 10, fastener members 344 may include other structures than aperture 346 to couple with force transmission mechanism 310, such as a groove or depression instead of an aperture. Further, instead of having a female mating feature with the chassis fastener having the complementary male mating feature, the positioning of the female and male mating features could be reversed.

Sterile adapters in accordance with various exemplary embodiments can include one or more structures for releasably coupling the sterile adapters to a manipulator arm of a patient side cart, such as an actuation interface assembly of a manipulator arm. As shown in the exemplary embodiment of FIG. 10, sterile adapter 340 includes one or more coupling member(s) 370 to couple sterile adapter 340 to a manipulator arm, such as to actuation interface assembly 122 of one of manipulator arms 110-113 in FIG. 1. According to an exemplary embodiment, a coupling member 370 is connected to fastener member 344. In this way, fastener member 344 and coupling member 370 can act in concert when releasing sterile adapter 340 from the manipulator arm, as will be discussed in further below.

Chassis 320 can include one or more structures to couple chassis 320 and sterile adapter 340 to one another. As shown in the exemplary embodiment of FIG. 4, chassis 320 comprises chassis fastener members 326 to couple chassis 320 with sterile adapter fastener members 344. Chassis fastener members 326 include, for example, an aperture 327 through which sterile adapter fastener members 344 are inserted from beneath chassis 320, such as along the direction indicated by arrow 329 in the exemplary embodiment of FIG. 4. Sterile adapter fastener members 344 are inserted through apertures 327 until protrusions 328 of chassis fastener members 326 are inserted within apertures 346. The chassis fastener members 326 are flexible tab structures that are biased slightly outwardly to provide a positive registration of the protrusions 328 in the apertures 346. As the protrusions 328 ride against the surface of sterile adapter fastener members 344, the fastener members 344 are pushed slightly outward until the protrusions 328 reach the apertures 346, at which point a snap-fit type of engagement occurs between the protrusions 328 and the apertures 346 to couple sterile adapter 340 and chassis 320 to one another. Such a connection may be made between each corresponding chassis fastener member 326 and sterile adapter fastener member 344.

Figure 11:
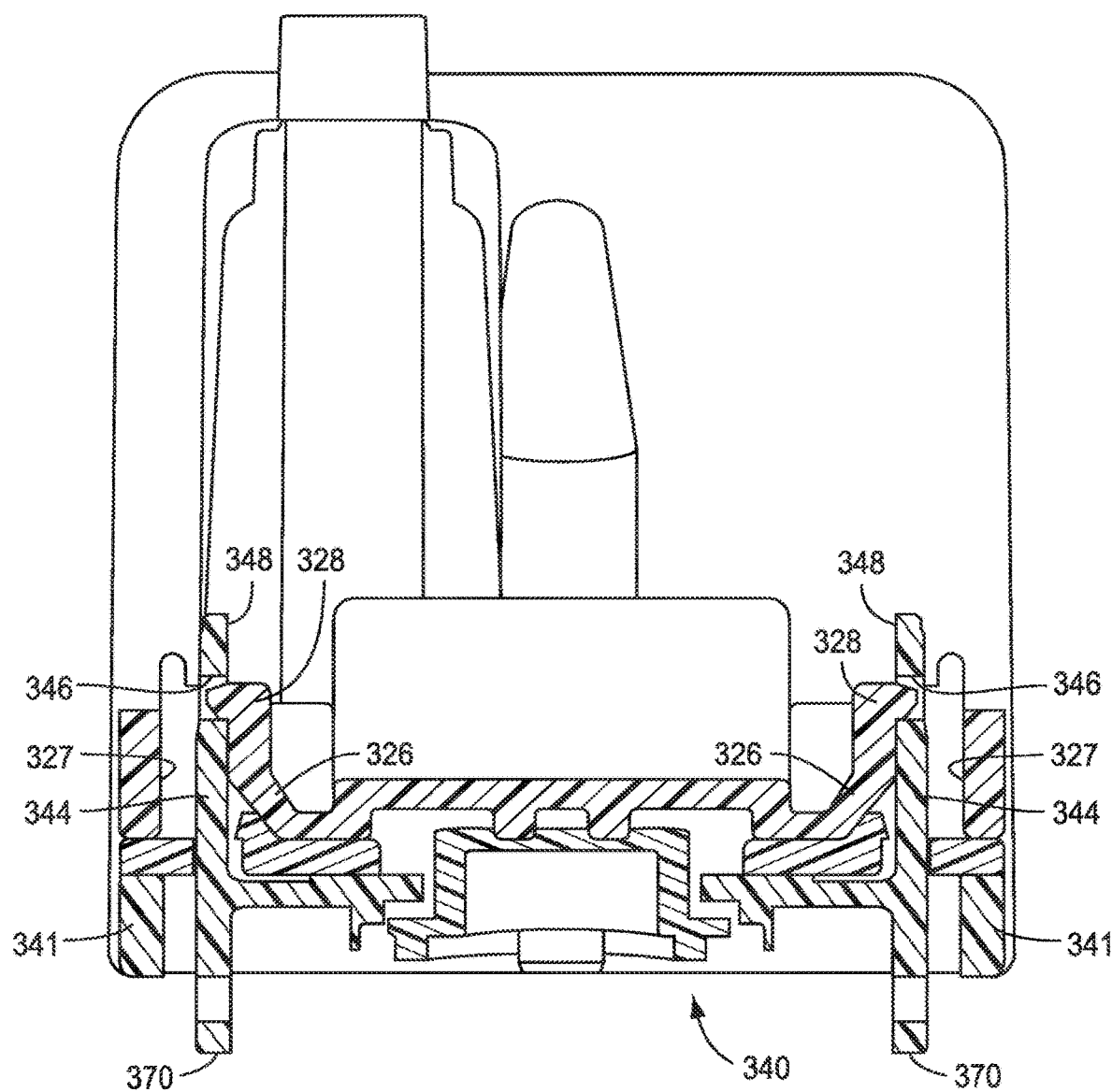
FIG. 11 is a cross-sectional view taken along line 11-11 in FIG. 8, with the housing of the force transmission mechanism not shown.

With reference to FIG. 11, which depicts a cross-section view of chassis 320 and sterile adapter 340 in a coupled state (with housing 330 of force transmission mechanism 310 being omitted in FIG. 11 for ease of illustration), sterile adapter fastener member 344 is fully inserted within aperture 327 so that protrusion 328 of chassis fastener member 326 is inserted within aperture 346. A surface 348 of sterile adapter fastener member 344 extends above chassis fastener member 326, including protrusion 328 of chassis fastener member 326, so that surface 348 is exposed when housing 330 is not coupled to chassis 320, as shown in the exemplary embodiment of FIG. 11. When chassis 320 and sterile adapter 340 are coupled to one another, as shown in FIG. 11, chassis 320 and sterile adapter 340 may be uncoupled by pressing against each sterile adapter fastener member 344, which disengages protrusion 328 from aperture 346 so sterile adapter fastener members 344 may be withdrawn from apertures 327 of chassis 320, as will be discussed below.

Force transmission mechanisms for surgical instruments may be designed with a mechanism for releasably coupling the force transmission mechanism to a drive interface device, such as, for example, directly to the actuation interface assembly (e.g., of a patient side cart) and/or to a sterile adapter, in order to permit relatively easy mounting and removal of a surgical instrument to a manipulator of a patient side cart. In accordance with various exemplary embodiments, at least a portion of the releasable coupling mechanism is designed to be part of the force transmission mechanism housing. Such placement of a releasable coupling mechanism as part of the housing frees up space on the chassis itself to be used, for example, for other force transmission mechanism components (e.g., gears, capstans, linkages, etc.). Moreover, in accordance with various exemplary embodiments, force transmission mechanism housings incorporating such coupling mechanisms can have a monolithic construction, permitting the housing and releasable coupling mechanisms to be molded as a single piece. The ability to provide a releasable coupling mechanism moldable with the housing (e.g., as a monolithic, single piece) can provide for robust manufacturing of a surgical instrument since the housing is already a component that is being made, for example, via molding. Thus, a reduction in the number of separate parts to be manufactured and later combined in an assembly can be realized, according to various exemplary embodiments.

Figure 7:
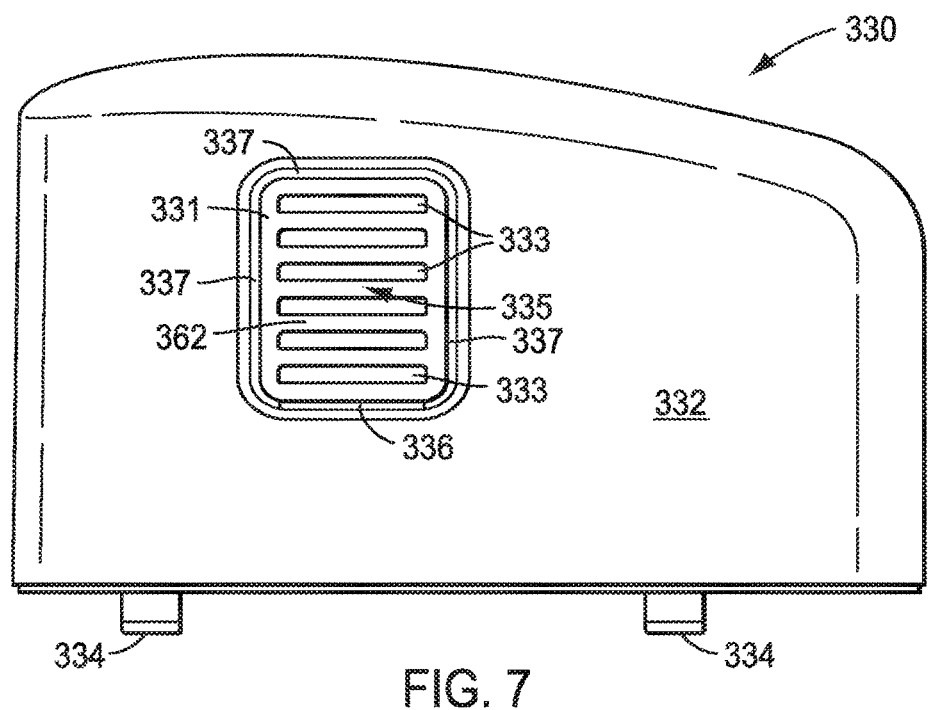
FIG. 7 is a side view of the housing of FIG. 6.
Figure 12:
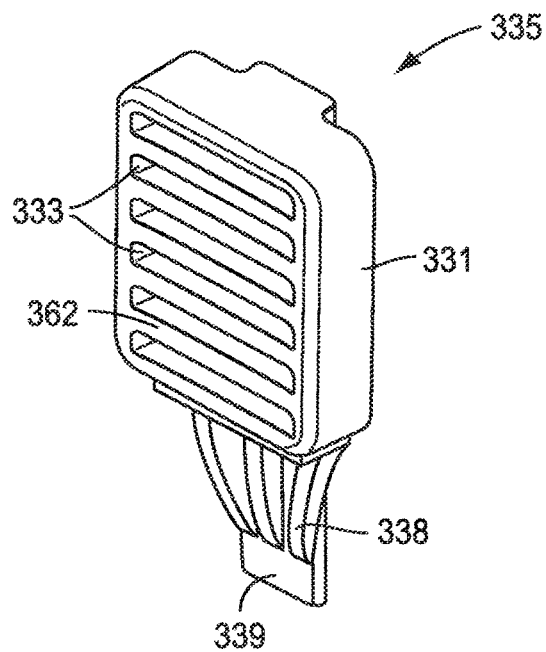
FIG. 12 is a perspective view of a releasable coupling mechanism of a force transmission mechanism, according to an exemplary embodiment.
Figure 13:
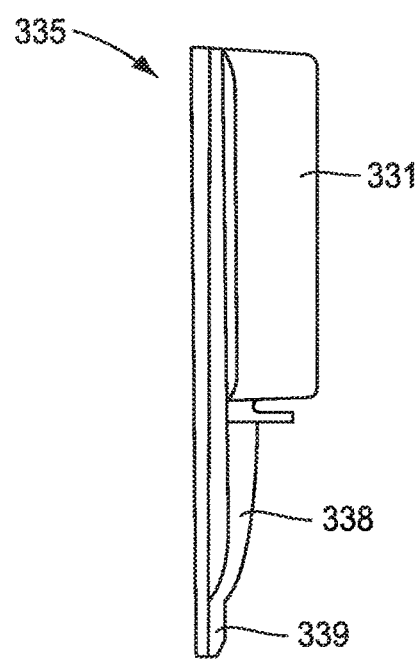
FIG. 13 is a side view of the releasable coupling mechanism of FIG. 12.

One exemplary embodiment of a releasable coupling mechanism 335 incorporated into housing 330 is illustrated in FIGS. 6 and 7. As shown in the exemplary embodiment of FIGS. 6 and 7, releasable coupling mechanism 335 has a single piece (i.e., monolithic) construction with side wall 332 of housing 330. FIGS. 12 and 13 depict releasable coupling mechanism 335 in isolation.

As shown in the exemplary embodiment of FIGS. 12 and 13, releasable coupling mechanism 335 includes a push-button portion 331 and a lever 338 extending from push-button portion 331. Lever 338 includes a surface 339 to engage fastener member 344 of sterile adapter 340, as will be discussed below. Push-button portion 331 comprises a surface 362 disposed to face outwardly from the housing 330. In various exemplary embodiments, the surface 362 is configured to provide a comfortable and functional gripping surface for a user, such as for a user's thumb and finger to enable a single-handed grasping of the housing during coupling and removal of a surgical instrument to a drive interface component. Accordingly, in the exemplary embodiment depicted, push-button portion 331 has a generally elongated shape (e.g., rectangular) and is generally sized to be slightly larger than an adult person's thumb or fingertip. However, those having ordinary skill in the art would appreciate that other shapes for push-button portion 331, such as, for example, square, circular, oval, and other shapes and sizes also may be used and are contemplated as being within the scope of the present disclosure.

As can be seen in FIG. 12, surface 362 of push-button portion 331, which faces outwardly, can be at least slightly concave to provide comfort and a natural surface to receive the generally convex surface of a tip of a thumb and/or finger. In addition, surface 362 of push-button portion 331 can optionally include various surface gripping features to assist in preventing slipping during grasping manipulation of the releasable coupling mechanisms by a user. Suitable gripping features can include a roughened surface, a knurled surface, a dimpled surface, and other suitable surface features to enhance grasping. In the exemplary embodiment depicted in the figures, the gripping features include one or more recesses, such as a series of recesses 333 extending along surface 362 in a direction generally perpendicular to a longitudinal direction of the releasable coupling member 335 (although it is contemplated as within the scope of the present disclosure that the recesses could extend in the longitudinal direction). The recesses 333 are spaced apart and separated by surface regions. In addition to providing a gripping feature on push-button portion 331 by the surface regions separating the recesses 333, recesses 333 facilitate molding of releasable coupling mechanism 335 by providing substantially uniform wall thicknesses in push-button portion 331, which in turn can assist in achieving substantially uniform material shrinkage in push-button portion 331 during a molding process to produce an aesthetically pleasing surface for push-button portion 331.

Figure 16:
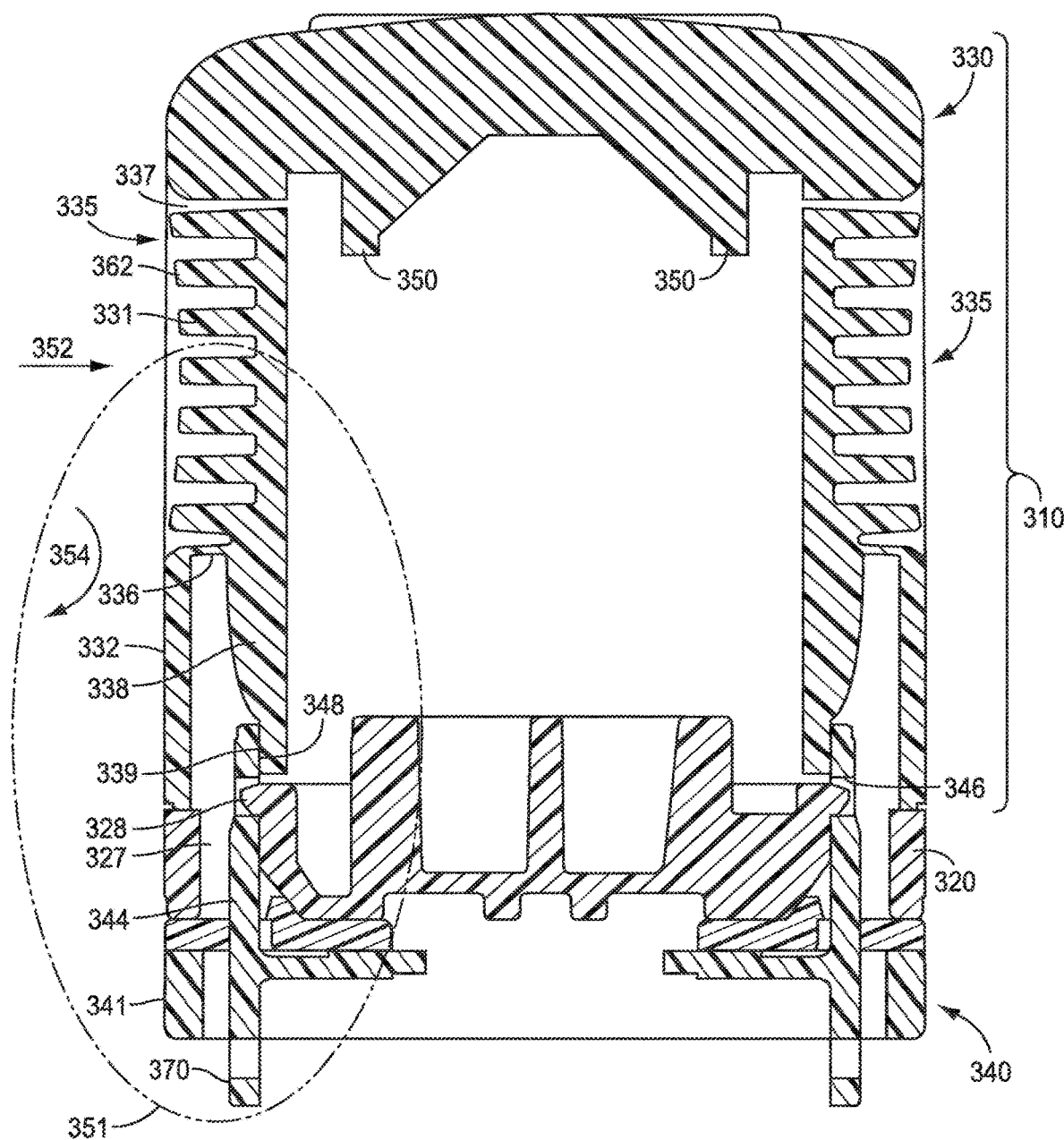
FIG. 16 is a cross-sectional view along line 16-16 of FIG. 14.

According to an exemplary embodiment, releasable coupling mechanism 335 is structured to pivot relative to side wall 332 of housing 330. For example, releasable coupling mechanism 335 is connected to side wall 332 via a structure that permits relative movement between the coupling mechanism 335 and the side wall 332. As a result, portions of releasable coupling mechanism 335 (e.g., lever 338 and surface 339) may pivot relative to side wall 332. Releasable coupling mechanism 335 and side wall 332 may be connected via a wall member 336, as shown in FIG. 16. Wall member 336 is, for example, a portion of housing 330 bridging side wall 332 and releasable coupling mechanism 335. According to an exemplary embodiment, wall member 336, side wall 332, and releasable coupling mechanism 335 have a single-piece (i.e., monolithic) construction. For instance, side wall 332, wall member 336, and releasable coupling mechanism 335 are formed as different parts of a single, continuous wall of housing 330 that vary in shape and/or thickness. According to another exemplary embodiment, wall member 336 is a separate part molded into housing 330, such as, for example, a metal strip molded into housing 330. As shown in the exemplary embodiment of FIG. 16, wall member 336 is located approximately between push-button portion 331 and lever 338. Wall member 336 may be relatively thin, such as in comparison to side wall 332 and/or releasable coupling mechanism 335, according to an exemplary embodiment. Thus, wall member 336 may be a thin portion of side wall 332 that acts as a hinge to permit releasable coupling mechanism 335 to move relative to (e.g., pivot relative to axis 360 shown in FIG. 17) side wall 332. As shown in the exemplary embodiment of FIG. 17, pivot axis 360 is approximately perpendicular to a longitudinal axis of releasable coupling mechanism 335.

Figure 15:
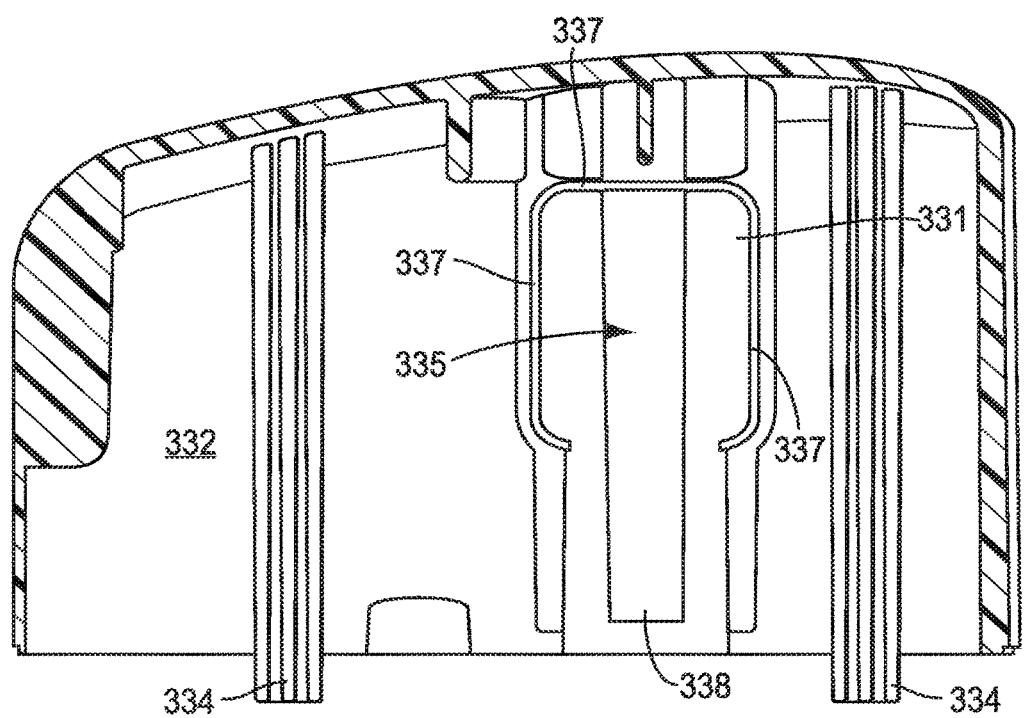
FIG. 15 is a cross-sectional view along line 15-15 of FIG. 14.

To allow releasable coupling mechanism 335 to move relative to side wall 332, housing 330 may comprise an open space between releasable coupling mechanism 335 and side wall 332 in which releasable coupling mechanism 335 and side wall 332 are not connected. As perhaps best shown in FIGS. 7 and 15, for example, housing 330 may include a gap 337 between releasable coupling mechanism 335 and side wall 332.

Gap 337 may be formed as an open space between releasable coupling mechanism 335 and side wall 332, for example, during the molding process to manufacture housing 330. As shown in the exemplary embodiment of FIG. 7, push-button portion 331 of releasable coupling mechanism 335 forms part of side wall 332, with gap 337 delineating a boundary between side wall 332 and push-button portion 331. According to an exemplary embodiment, gap 337 and wall member 336 are shaped so that releasable coupling mechanism 335 is connected to (has a single piece (i.e., monolithic) construction with) side wall 332 (e.g., via wall member 336) on only one side of releasable coupling mechanism 335, as shown in FIG. 7. For example, releasable coupling mechanism 335 is connected to side wall 332 on only one side of releasable coupling mechanism 335 via wall member 336.

With reference to FIG. 16, the operation of releasable coupling mechanism 335 will be described. FIG. 16 depicts housing 330, chassis 320, and sterile adapter 340 in a connected state. For instance, housing 330 and chassis 320 is connected via housing connector structures 334 and 324 (not shown in FIG. 16) and chassis 320 and sterile adapter 340 are connected via insertion of complementary fastener members 344 and 326, as also shown in FIG. 16 and described above. Further, releasable coupling mechanism 335 may be in contact with sterile adapter fastener member 344. For instance, lever 338 of releasable coupling mechanism 335 is in contact with fastener member 344, such as by surface 339 of lever 338 being in contact with surface 348 of sterile adapter fastener member 344, as depicted in the exemplary embodiment of FIG. 16.

To actuate releasable coupling mechanism 335, a user depresses push-button portion 331. For example, a user presses against push-button portion 331 along the general direction indicated by arrow 352 in the exemplary embodiment of FIG. 16. The applied force in turn causes releasable coupling mechanism 335 to move relative to side wall 332. That is, releasable coupling mechanism 335 pivots and thus partially rotates relative to side wall 332 along the direction indicated by arrow 354 (e.g., about axis 360 in FIG. 17). As shown in the exemplary embodiment of FIG. 16, housing 330 includes two releasable coupling mechanisms 335 disposed on opposing sides of housing 330 and generally aligned with each other. Arranging the releasable coupling mechanisms 335 in this manner permits a user to grasp and actuate both releasable coupling mechanisms 335 with a single hand (e.g., via a thumb and forefinger of a single hand). However, the various exemplary embodiments described herein are not limited to the configuration shown in FIG. 16 and may include other numbers and arrangements of releasable coupling mechanisms.

Figure 17:
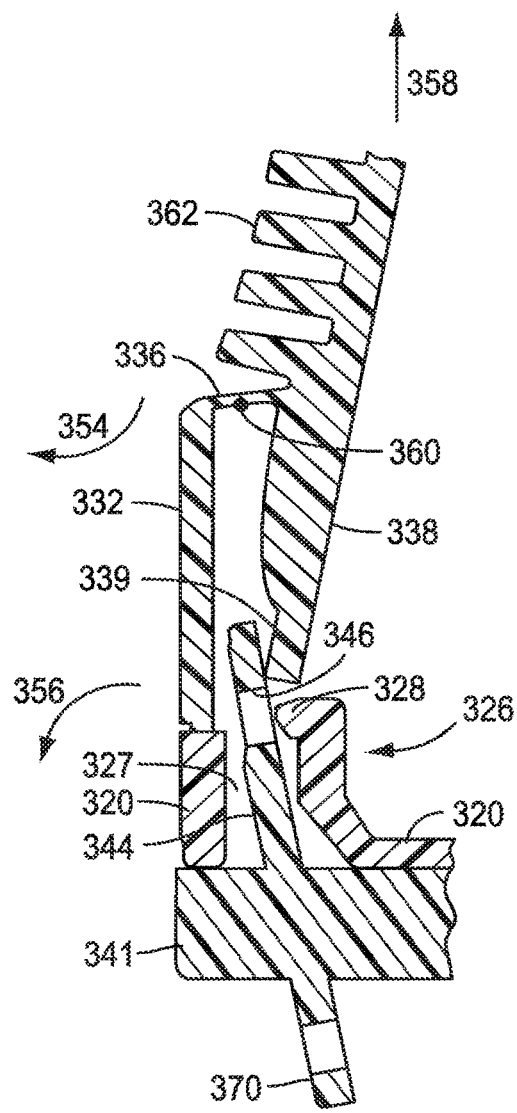
FIG. 17 is a detailed view of a portion 351 of FIG. 16 with a chassis and a sterile adapter in a disconnected state.

As releasable coupling mechanism 335 moves relative to side wall 332 by rotating along direction 354, lever 338 presses against sterile adapter fastener member 344. For instance, surface 339 of lever 338 presses against surface 348 of fastener member 344. Turning to FIG. 17, portion 351 of FIG. 16 is shown in a state after releasable coupling mechanism 335 has moved relative to side wall 332 along direction 354. As a result, lever 338 also pivots along direction 354, causing lever 338 to press against sterile adapter fastener member 344, such as by pressing surface 339 of lever 338 against surface 346 of fastener member 344. As lever moves along direction 354, fastener member 344 is forced by lever 338 to move relative to base 341 of sterile adapter 340 and relative to chassis 320. In particular, fastener member 344 pivots along the direction indicated by arrow 356 in FIG. 17. This movement disengages sterile adapter fastener member 344 from chassis fastener member 326 by releasing protrusion 328 of chassis fastener member 326 from aperture 346 of sterile adapter fastener member 344. With the fastener members 326 and 344 disengaged from each other, force transmission mechanism 310 may be removed from sterile adapter 340, such as by withdrawing force transmission mechanism 310 along direction 358 in FIG. 17 to in turn withdraw fastener member 344 through aperture 327 of fastener member 326.

In an exemplary embodiment, a reaction force is produced when sterile adapter fastener member 344 and chassis fastener member 326 are being released from one another, causing chassis 320 and housing 330 to be pushed away from sterile adapter 340 along direction 358. As a result, the surgical instrument is pushed away from the sterile adapter 340. Further, in an exemplary embodiment, an audible noise also is created when sterile adapter fastener member 344 and chassis fastener member 326 are being released from one another, such as, for example, due to recovery of one or more of the sterile adapter fastener member 344 and chassis fastener member 326 from an elastically deformed state. Such feedback can confirm to a user that the surgical instrument has been disengaged.

According to an exemplary embodiment, release of chassis fastener member 326 from sterile adapter fastener member 344 does not release the sterile adapter 340 from a manipulator arm the sterile adapter 340 is coupled to. For example, a connection between the sterile adapter 340 and a manipulator arm require rotating the sterile adapter 340 relative to the manipulator arm (e.g., such as along direction 354 in FIG. 17) in order to release or connect the sterile adapter to the manipulator arm. However, connections between the sterile adapter 340 and a manipulator arm are not limited to this embodiment and may include other connection mechanisms for connecting the sterile adapter 340 to a manipulator arm. According to an exemplary embodiment, actuation of releasable coupling mechanism 335 actuates a coupling member 370 to release sterile adapter 340 from a manipulator arm the sterile adapter 340 is coupled to. As discussed in the exemplary embodiment above, coupling member 370 is connected to a fastener member 344 of sterile adapter 340. As depicted in the exemplary embodiment of FIG. 16, fastener member 344 and coupling member 370 have, for example, a single-piece, monolithic construction. When fastener member 344 is forced to move due to actuation of releasable coupling mechanism 335, as discussed above, coupling member 370 also moves relative to housing 330 by pivoting along the direction indicated by arrow 356 in the exemplary embodiment of FIG. 17. As a result, coupling member 370 is disengaged from a corresponding fastener (not shown) of a manipulator arm and sterile adapter 340 also is released from the manipulator arm.

Figure 14:
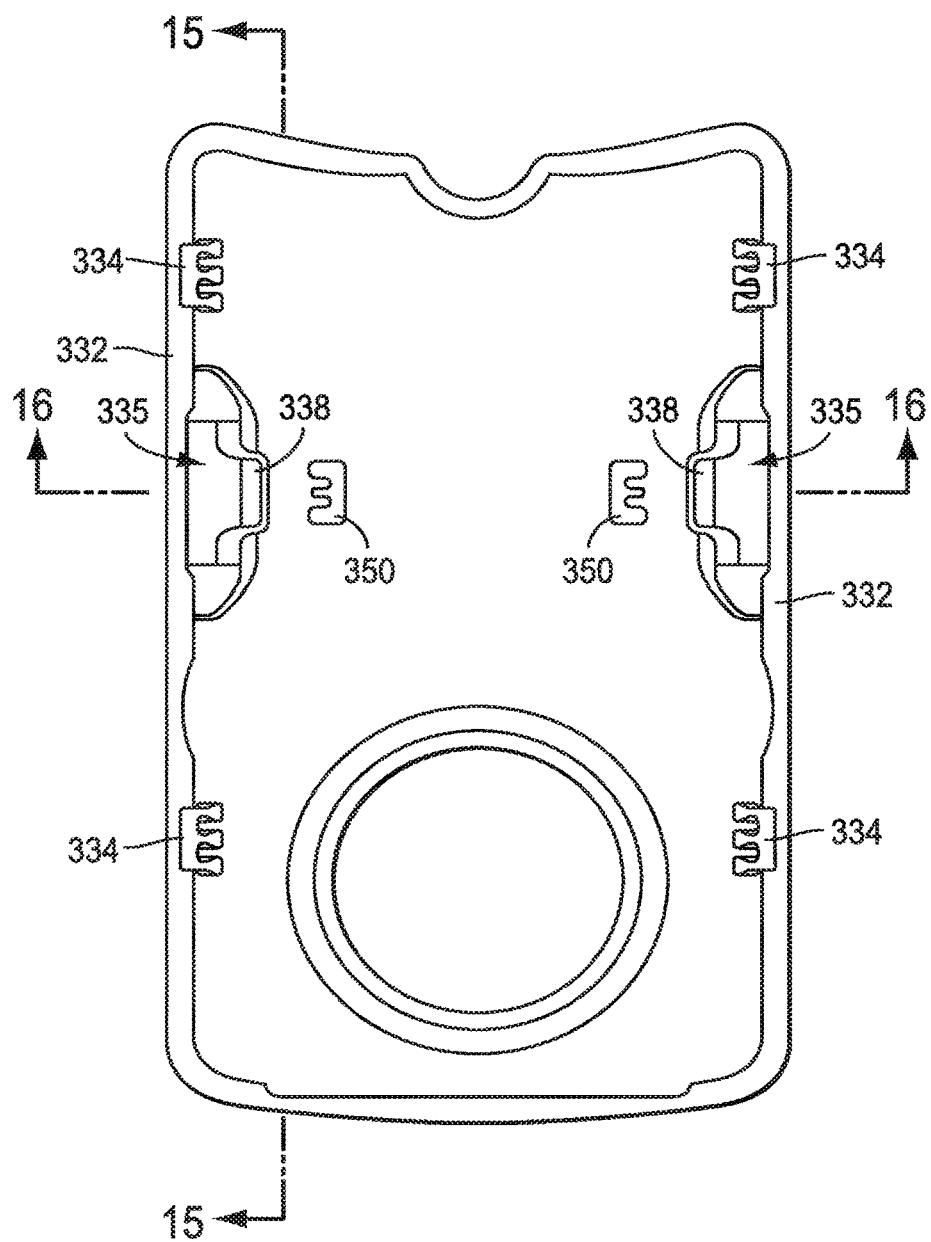
FIG. 14 is a bottom view of the housing of FIG. 6.

A housing of a force transmission mechanism may include one or more structures to limit the movement of a releasable coupling mechanism, for example, to prevent damage to the releasable coupling mechanism and/or other portions of the force transmission mechanism or a drive interface component. According to an exemplary embodiment, housing 330 includes a stop 350, as shown in FIGS. 14 and 16. Stop 350 is structured to arrest movement of releasable coupling mechanism 335 relative to side wall 332 due to releasable coupling mechanism 335 contacting stop 350 when releasable coupling mechanism 335 pivots relative to side wall 332. Housing 330 may include a stop 350 positioned so as to correspond to each releasable coupling mechanism 335. Stop 350 may be positioned relative to releasable coupling mechanism 335 to limit movement of releasable coupling mechanism 335. For example, stop 350 limits movement of releasable coupling mechanism 335 so that when a user actuates releasable coupling mechanism 335, such as by depressing push-button portion 331 of releasable coupling mechanism 335, lever 338 of releasable coupling mechanism 335 is moved a limited amount due to engagement with stop 350. Thus, when a chassis 320 or sterile adapter 340 is connected to housing 330, contact between components of chassis 320 or sterile adapter 340 (e.g., fastener member 344) and lever 338 is minimized or prevented. As a result, damage to releasable coupling mechanism 335 is minimized or prevented due to the contact.

As described above, releasable coupling mechanism 335 may have a single-piece, monolithic construction with side wall 332 of housing 330. This is further illustrated in FIG. 14, which is a bottom view revealing an interior of housing 330, with releasable coupling mechanism 335 shown as part of side wall 332. Housing 330 can be manufactured, for example, via a molding process. Such a molding process advantageously provides housing 330 and releasable coupling mechanism 335 with a single-piece, monolithic construction. Such a construction that allows the releasable coupling mechanism to be part of the housing 330, in particular as a monolithic configuration, is beneficial in that the number of parts to be manufactured in separate processes can be reduced and/or because little or no finishing may be needed after molding is complete. According to various exemplary embodiments, housing 330 is molded from a polymer material. For example, housing is molded from polycarbonate, polycarbonate comprising glass filler (e.g., about 8-10% by weight glass filler), and other materials familiar to one of ordinary skill in the art.

Figure 18:
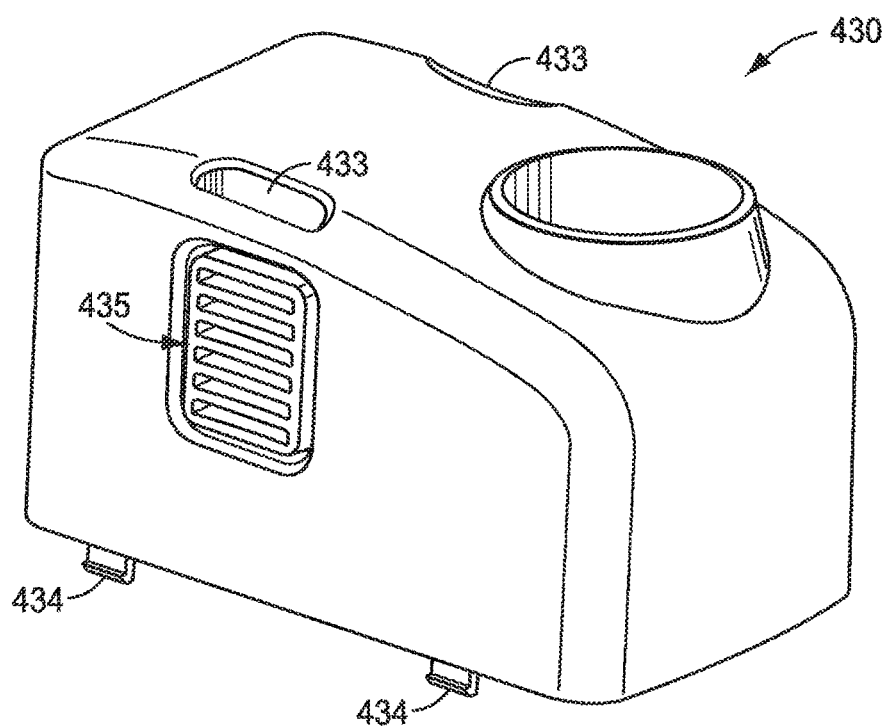
FIG. 18 is a housing of a force transmission mechanism, according to another exemplary embodiment.

The various exemplary embodiments in accordance with the present disclosure may utilize configurations other than those described above. For example, various components of a force transmission mechanism include recesses to facilitate molding of the components, such as to provide substantially uniform wall thickness to facilitate substantially uniform material shrinkage during molding, as discussed above with regard to push-button portion 331 of releasable coupling mechanism 335. Turning to FIG. 18, an exemplary embodiment of a housing 430 for a force transmission mechanism is shown. Housing 430 comprises a releasable coupling mechanism 435 and one or more fasteners 434 to couple housing 430 to a chassis (not shown) of a force transmission mechanism, as described above with regard to the exemplary embodiment of FIGS. 3-17. Housing 430 may further comprise one or more recesses 433 to provide a substantially uniform wall thickness for housing 430, thus facilitating molding of housing 430.

Although various exemplary embodiments have been described herein regarding the releasable coupling facilitating coupling of a force transmission mechanism to a sterile adapter, such as when the sterile adapter is disposed between the force transmission mechanism and an actuation interface assembly of a manipulator, the releasable coupling of the various exemplary embodiments described herein is not limited to coupling a force transmission mechanism of an instrument to a sterile adaptor. For example, the various exemplary embodiments further contemplate the releasable coupling facilitating coupling of the force transmission mechanism directly to an actuator, such as to directly couple a force transmission mechanism to an actuation interface assembly of a manipulator arm of a patient side cart, or to another actuator providing drive forces to actuate an instrument.

Providing force transmission mechanisms that incorporate releasable coupling mechanisms with the housing of a force transmission mechanism can facilitate manufacture and design of surgical instruments. In particular, providing releasable coupling mechanisms, according to the configurations disclosed herein, permits a housing incorporating those mechanisms to be made, e.g., via molding, as a single-piece, monolithic structure, which may be desirable to provide robust manufacturing of a surgical instrument, to reduce the number of separately manufactured parts, and/or to leave room for parts on the chassis of a force transmission mechanism.

The exemplary embodiments and methods described herein have been described as being utilized with surgical instruments for teleoperated surgical systems. However, the exemplary embodiments and methods described herein may be used with other surgical devices, such as laparoscopic instruments and other hand held instruments. Further, the exemplary embodiments and methods may be employed in other application that use remotely actuatable wrist or multiple joint structures, such as to remotely position an object attached to the wrist or joint structures. For example, the exemplary embodiments and methods of various exemplary embodiments described herein may be used in various nonsurgical fields, such as, for example, exploration, oil extraction, and other fields using remotely actuatable structures.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the claims being entitled to their full breadth and scope, including equivalents.

What is claimed is:

1. A force transmission mechanism of a surgical instrument, the force transmission mechanism being configured to releasably engage with a drive interface device of a teleoperated surgical system, the force transmission mechanism comprising:
    a housing comprising an exterior and an interior;
    one or more drive components in the interior of the housing; and
    a releasable coupling mechanism configured to releasably engage the force transmission mechanism with the drive interface device;
    wherein the releasable coupling mechanism comprises:
        an actuator portion accessible from the exterior of the housing, and
        a lever in the interior of the housing; and
    wherein the lever is moveable to release engagement of the force transmission mechanism from the drive interface device.

2. The force transmission mechanism of claim 1, wherein:
    the actuator portion is a push-button in a wall of the housing.

3. The force transmission mechanism of claim 1, wherein:
    the lever comprises a first end and a second end opposite the first end;
    the first end is coupled to the actuator portion; and
    the second end is configured to releasably engage a fastener member of the drive interface device.

4. The force transmission mechanism of claim 1, wherein:
    the force transmission mechanism further comprises a chassis;
    the chassis comprises at least one interface structure configured to engage with the drive interface device;
    the at least one interface structure is operably coupled to an actuation element; and
    the actuation element is configured to transmit force to a distal end portion of the surgical instrument.

5. The force transmission mechanism of claim 4, wherein:
    the chassis and the housing are configured to be removably coupled to each other.

6. The force transmission mechanism of claim 4, wherein:
    the chassis and the housing have a monolithic construction.

7. The force transmission mechanism of claim 4, wherein:
    the drive interface device is a sterile adapter comprising at least one interface drive mechanism configured to engage with an output drive of a teleoperated manipulator; and
    the at least one interface structure of the chassis is configured to engage the interface drive mechanism to receive forces transmitted from the output drive through the interface drive mechanism.

8. The force transmission mechanism of claim 1, wherein:
    the releasable coupling mechanism further comprises a hinge connecting the actuator portion and the lever.

9. The force transmission mechanism of claim 8, wherein:
    the hinge, the actuator portion, and the housing have a monolithic construction.

10. The force transmission mechanism of claim 1, wherein:
    the lever is pivotable relative to the housing in response to actuation of the actuator portion.

11. The force transmission mechanism of claim 1, wherein:
    the housing comprises a first side and a second side opposite the first side;
    the releasable coupling mechanism is a first releasable coupling mechanism and is located on the first side of the housing;
    the force transmission mechanism further comprises a second releasable coupling mechanism located on the second side of the housing; and
    the first and second releasable coupling mechanisms are arranged to permit grasping by a thumb on the first releasable coupling mechanism and a finger on the second releasable coupling mechanism.

12. The force transmission mechanism of claim 1, wherein:
    the housing comprises a stop to limit movement of the lever toward the interior of the housing.

13. The force transmission mechanism of claim 1, wherein:
    in an engaged state of the force transmission mechanism with the drive interface device, the force transmission mechanism is operably coupled to receive an input drive force from the teleoperated surgical system.

14. A method of releasing a force transmission mechanism of a surgical instrument from a drive interface device of a manipulator arm of a teleoperated surgical system, the method comprising:
    actuating, from an exterior of a housing of the force transmission mechanism, a release actuator mechanism for the surgical instrument;
    causing, in response to the actuating, a lever in an interior of the housing of the force transmission mechanism to disengage the drive interface device from the force transmission mechanism; and
    removing the force transmission mechanism from the drive interface device.

15. The method of claim 14, wherein:
    the release actuator mechanism is a push button; and
    the actuating comprises depressing the push button.

16. The method of claim 14, wherein:
    the release actuator mechanism is coupled to a first portion of the lever; and
    causing the lever in an interior of the housing of the force transmission mechanism to disengage the drive interface device from the force transmission mechanism comprises engaging a second portion of the lever against a fastener member of the drive interface device.

17. The method of claim 14, wherein:

causing the lever in the interior of the housing of the force transmission mechanism to disengage the drive interface device from the force transmission mechanism comprises pivoting the lever relative to the housing.

18. The method of claim 14, wherein:

causing the lever in the interior of the housing of the force transmission mechanism to disengage the drive interface device from the force transmission mechanism comprises pivoting the lever about a hinge integrally formed with the lever and the housing.

19. The method of claim 14, wherein:

removing the force transmission mechanism from the drive interface device comprises disengaging an interface structure of the force transmission mechanism from the drive interface device; and the interface structure is operably coupled to an actuation member of the surgical instrument.

20. The method of claim 14, wherein:

the method further comprises limiting movement of the lever by abutting the lever against a stop.

* * * * *